United States Patent [19]

Zweig

[11] Patent Number: 5,554,531
[45] Date of Patent: Sep. 10, 1996

[54] DEVICE FOR PERFORMING TIMED ASSAY BY ELECTRICAL RESISTANCE CHANGE

[75] Inventor: Stephen E. Zweig, Los Gatos, Calif.

[73] Assignee: Avocet Medical, Inc., Los Gatos, Calif.

[21] Appl. No.: 512,134

[22] Filed: Aug. 7, 1995

Related U.S. Application Data

[63] Continuation of Ser. No. 267,051, Jun. 17, 1994, abandoned, and a division of Ser. No. 3,771, Jan. 13, 1993, Pat. No. 5,344,754.

[51] Int. Cl.$^6$ ................................................. G01N 21/01
[52] U.S. Cl. .................... 435/286.1; 435/287.1; 435/287.7; 435/288.7; 422/56; 436/46; 436/808; 204/777.5
[58] Field of Search ...................... 435/4, 817, 286.1, 435/287.1, 287.7, 287.9, 288.7; 436/46, 805, 806, 808; 422/56; 204/513.12

[56] References Cited

U.S. PATENT DOCUMENTS

| | | | |
|---|---|---|---|
| 3,663,374 | 5/1972 | Moyer et al. | 195/103.5 R |
| 3,791,933 | 2/1974 | Moyer et al. | 195/127 |
| 3,826,734 | 7/1974 | Godsey | 204/299 |
| 4,038,030 | 7/1977 | Albright et al. | 23/230 B |
| 4,053,381 | 10/1977 | Hamblen et al. | 204/195 M |
| 4,171,246 | 10/1979 | Hamblen et al. | 204/1 T |
| 4,219,529 | 8/1980 | Tersteeg et al. | 422/65 |
| 4,256,693 | 3/1981 | Kondo et al. | 422/56 |
| 4,366,241 | 12/1982 | Tom et al. | 435/7 |
| 4,420,566 | 12/1983 | Jessop et al. | 436/46 |
| 4,720,372 | 1/1988 | Fey et al. | 422/67 |
| 4,849,340 | 7/1989 | Oberhardt | 435/13 |
| 4,911,794 | 3/1990 | Parce et al. | 204/1 T |
| 4,935,346 | 6/1990 | Phillips et al. | 422/68.1 |
| 5,049,487 | 9/1991 | Phillips et al. | 435/14 |
| 5,059,394 | 10/1991 | Phillips et al. | 435/4 |
| 5,059,525 | 10/1991 | Bartl et al. | 435/13 |
| 5,418,143 | 5/1995 | Zweig | 435/13 |

FOREIGN PATENT DOCUMENTS 1318815  5/1973  United Kingdom .

OTHER PUBLICATIONS

Foulds, N. C., et al., "Rapid Electrochemical Assay for Theophylline in Whole Blood Based on the Inhibition of Bovine Liver Alkaline Phosphatase," *Analytica Chimica Acta* 229 (1990) pp. 57–62.

*Primary Examiner*—Esther Kepplinger
*Assistant Examiner*—Milton I. Cano
*Attorney, Agent, or Firm*—Townsend and Townsend and Crew

[57] ABSTRACT

Assays for liquid analytes are performed on a bibulous matrix containing dried reagents which produce a visibly detectable reaction product. Application of liquid sample to the bibulous matrix is detected by measuring a drop in resistance across the matrix. A preferred test article for performing the method includes the matrix and a pair of spaced-apart electrodes in electrical contact with a reaction zone on the matrix. The test article is used in combination with a detection unit having means for probing the electrodes to determine when electrical resistance in the matrix has decreased. The assay methods and apparatus are particularly useful for performing enzyme assays where signal developed as a function of time is critical.

12 Claims, 3 Drawing Sheets

DEVICE FOR PERFORMING TIMED ASSAY BY ELECTRICAL RESISTANCE CHANGE

This invention was made with government support under SBIR Grant No. 1 R43 HL48978-01 awarded by the National Institutes of Health. The government has certain rights in the invention.

This is a continuation of application No. 08/267,051, filed Jun. 17, 1994, now abandoned, and a division of application No. 08/003,771, filed Jan. 13, 1993, now U.S. Pat. No. 5,344,754.

BACKGROUND OF THE INVENTION

1. Field of the Invention

The present invention relates generally to methods and apparatus for detecting analytes in liquid samples. More particularly, the present invention relates to assays for detecting enzymes and components of enzyme pathways where both the time and temperature of the assay are controlled.

Enzymes and enzymatic pathways play an important role in medicine and are the subject of many clinical tests. Examples of tests for single enzymes include tests for amylase, creatine kinase, alanine aminotransferase, aspartate aminotransferase, streptokinase, and thrombin. Examples of tests for enzymatic pathways include the prothrombin time test, and the activated partial thromboplastin time test. These later tests measure the enzymatic pathways involved in the extrinsic and intrinsic blood coagulation systems.

Tests involving enzymatic reactions tend to be technically demanding. Enzymes and enzymatic pathways are typically assayed by measuring the rate at which the enzyme or enzymatic pathway in question converts a particular enzymatic substrate into its product. Such rate measurements require precise test timing since timing errors are directly translated into errors in the calculated amount of enzyme or component in an enzyme pathway.

Temperature control is also critical since most enzymes have reaction rates that change dramatically as a function of temperature. Typically, higher temperatures produce a higher reaction rate, and lower temperatures produce a lower reaction rate. Enzymatic pathways, consisting of a number of temperature sensitive enzymatic steps, are often extremely temperature sensitive as a result of the cascade effect.

Because of these technical demands, most enzyme and enzymatic pathway tests have tended to be complex, with performance generally limited to clinical laboratories. While such centralized testing may be adequate for infrequent, or routine medical conditions, visiting a doctor's office or a clinic on a regular basis for frequent or emergency medical tests is less acceptable. Thus there exists a need for convenient and simple tests, that can be performed by unskilled users for the measurement of enzymes and enzyme pathways.

A variety of simplified "test-strip" assays have been developed to allow semi-skilled and unskilled users to detect analytes, such as pregnancy hormones, cholesterol, and glucose in urine, blood, and other patient samples. These test strip assays are most useful with non-enzymatic analytes where detection does not vary with minor fluctuations in test time or temperature. As previously discussed, enzymatic reactions are less tolerant, and require more precise control over these variables, generally rendering them unsuitable for use in the home or other non-clinical environment.

One such test strip for performing blood glucose analysis, available from LifeScan Inc., Milpitas, Calif., relies on applying a drop of blood to a polyamide membrane having impregnated reagents which produce a chromogenic reaction in response to the glucose level in applied blood. Simplified low-cost tests such as this are often referred to as "home tests" to designate the fact that they have achieved a price and simplicity level that would allow widespread adoption in non-professional settings.

For these reasons, it would be desirable to provide simplified assays, test articles, and test systems for detecting problematic analytes, such as enzymes and components of enzyme pathways in a variety of patient samples, such as blood, urine, and the like. In particular, the test articles and test systems should permit simplified assay protocols, preferably allowing for an automatic timing cycle which is initiated as soon as a sample is applied to a test article. The test articles and test systems should optionally also facilitate providing precise temperature control of a test region on the article, preferably without the need to enclose the test article in a heated chamber or other structure which limits the user access. The assays, test articles, and test systems should be readily usable with small sample volumes, particularly with small blood volumes such as a single blood drop. The test articles should further inhibit loss of the patient sample from the test article by evaporation or other means, particularly when using very small sample volumes. The test article and test system should still further provide for monitoring of the presence of sample within the test article and be able to warn the user when excessive amounts of sample have been lost. Such test articles and test systems should be both easy to manufacture and easy to use, preferably being producible at relatively low costs.

2. Description of the Background Art

Assay devices which detect the presence of an analyte based on the enzymatic conversion of a substrate to a visible or detectable product within an absorptive matrix are described in U.S. Pat. Nos. 5,059,525; 5,059,394; 4,256,693; 4,935,346; 3,791,933; and 3,663,374. Analytical apparatus having means for detecting sample application are described in U.S. Pat. Nos. 5,049,487 and 4,420,566. The '487 patent describes a timing circuit which is triggered by detecting a change in reflectance caused by wetting of a porous matrix. The '566 patent describes the measurement of light absorbance to confirm that a liquid sample has been applied to a slide prior to analysis. Systems for controlling the temperature of analytical test substrates are described in U.S. Pat. Nos. 4,720,372; 4,219,529; and 4,038,030. Analytical test substrates comprising ion selective electrodes are described in U.S. Pat. Nos. 4,171,246 and 4,053,381.

SUMMARY OF THE INVENTION

According to the present invention, apparatus and assays are provided for performing timed assays, particularly timed enzymatic assays under temperature control. The apparatus includes both a test article which receives a liquid sample being tested and a detection unit which receives the test article and optically determines a change in the test article resulting from presence of analyte in the sample over time. The observed change can thus be related to the presence (and usually amount) of analyte present in the sample. Such an apparatus permits performance of simplified assay protocols and formats where the application of sample to the test article present in the detection unit initiates a timing cycle and where the observed changes in the test article can then be detected as a function of time relative to the application of sample.

The test article comprises a bibulous matrix having one or more dried reagents present therein. The reagents are selected to produce a detectable signal in the presence of an analyte in a liquid sample applied to the matrix. A pair of spaced-apart electrodes are disposed on either side of a target location on the matrix so that application of a liquid sample to the target location will lower electrical resistance between the electrodes. In this way, initial sample application can be detected by monitoring the resistance across the electrodes, with a lowering of the resistance initiating a timing cycle in the detection unit. Additionally, a subsequent rise in electrical resistance between the electrodes may indicate that sample has evaporated or otherwise been lost from the-target location which can be a particular problem with relatively lengthy test protocols, particularly when employing small sample volumes.

The test article can further be designed to reduce evaporative loss of liquid sample. The spaced-apart electrodes will preferably be configured to leave only a narrow gap therebetween, and the remaining portions of the matrix surface(s) will be covered by other materials. Usually, at least a portion of the remaining covering will be transparent to permit optical assessment of the matrix of the test article during assay protocols as described in more detail hereinafter. With such a design, only the narrow gap between electrodes (which defines a target location for receiving sample) will remain uncovered, thus permitting liquid sample application but preventing significant evaporation from the bibulous matrix thereafter.

A preferred construction for the test article of the present invention will comprise a relatively thin membrane defining the bibulous matrix, a pair of spaced-apart metal foil strips defining the electrodes and covering substantially the entire top surface of the membrane, and a transparent layer or support, such as a clear plastic strip, covering the bottom surface of the membrane. Such a test article permits sample application on the top of the membrane through the gap between adjacent electrodes and further permits optical viewing of the membrane through the transparent bottom.

The detection unit of the present invention will include a support stage for receiving the test article so that a reaction zone on the test article is disposed at a viewing location within the detection unit. The detection unit further includes means for measuring the electrical resistance across the test article when the test article is in place on the support stage. Usually, the resistance detecting means will include a pair of plates or probes which contact the bibulous matrix on either side of the reaction zone (which is located at or near the target location), preferably comprising a pair of plates which contact the electrodes described above.

The detection unit, however, could be designed to function with test articles which do not include discrete electrodes. In particular, the detection unit could be designed to directly probe spaced-apart locations on the membrane surface. While such a design will generally be less preferred, it is considered to be within the broad scope of the present invention.

The detection unit will further comprise a heater for heating the test article approximate the reaction zone. In the exemplary embodiment, the heater will include heated plates which contact the metal foil electrodes on either side of the target location on the test article. The metal foil electrodes are thus able to transfer heat from the heated metal plates of the detection unit directly to the target location and reaction zone without blocking or obscuring the target zone for a sample application.

The detection unit still further includes optical viewing means for detecting an optical change in the reaction zone, typically through the transparent layer of the test article. In exemplary embodiments, the optical viewing means comprises a light source which directs light against the reaction zone and an optical detector which detects light emitted or reflected from the reaction zone.

According to the method of the present invention, a volume of a liquid sample is applied to the target location on a bibulous matrix, where the bibulous matrix comprises one or more dried reagents which in the presence of analyte initiate time-dependent production of a detectable signal. The precise time the sample is applied can be determined by measuring a change in electrical resistance across the target location on the matrix. Production of the detectable signal is then measured at one or more times after the resistance change is first detected. In this way, the timed-dependant production of the detectable signal can be carefully monitored over time and accurately related back to the presence in amount of analyte in the liquid sample.

DESCRIPTION OF SPECIFIC EMBODIMENTS

Assays according to the present invention are useful for detecting a wide variety of soluble analytes in virtually any type of biological or other sample which is liquid or which can be liquified. The methods and apparatus will find their greatest use with patient specimens, such as blood, serum, plasma, urine, cerebral fluid, spinal fluid, ocular lens liquid (tears), saliva, sputum, semen, cervical mucus, scrapings, swab samples, and the like, but might also find use with food, environmental, industrial, and other samples where substances can be detected using enzymatic, immunological, and similar techniques. The methods and apparatus of the present invention are particularly useful for detecting analytes in very small liquid samples, typically having a volume in the range from about 3 µl to 50 [l, usually from 5 µl to 30 µl, but will also be suitable for use with much larger samples. In particular, the methods and apparatus of the present invention will be useful for analyzing very small blood samples, typically comprising a single drop of blood, employing non-skilled or semi-skilled personnel, frequently being self-administered.

The methods and apparatus of the present invention are also particularly suited for performing enzymatic assays within a bibulous matrix where an analyte in a sample applied to the matrix initiates, modulates, or otherwise affects the enzymatic conversion of a substrate (initially dried within the matrix) into an optically detectable product, such as a colored, luminescent, or fluorescent product. The present invention provides for very accurate timing of such enzymatic reactions based on initiation of a timing cycle at the moment the liquid sample is initially applied to the test article. The test article and detection unit can further provide for accurate temperature control of the test article, further assuring accuracy of the test result.

Assays according to the present invention provide for sensing of sample addition to a test article by measuring electrical resistance across a portion of the bibulous matrix to which the sample is applied. As the bibulous matrix and all reagents present therein are initially in a dry state, the resistance of the bibulous matrix prior to sample addition will be relatively high. Application of a liquid sample will immediately lower the electrical resistance across that portion of the matrix to which it is applied, thus providing a marker or trigger for initiation of a timing cycle. In the case of enzymatic reactions, build-up of the optically detectable product will take some time and is usually highly dependent on the amount of analyte present within the sample (as well as other factors such as temperature). By providing control circuitry within or in combination with the detection unit, the amount of optically detectable product accumulating within the test article over time can be precisely determined. Based on one or more such data points, usually a plurality of such data points, the amount of analyte initially present in the sample can then be accurately calculated.

The detection unit of the present invention will comprise means for monitoring and measuring resistance across that portion of the test article to which liquid sample is to be applied. The resistance detecting circuitry will be connected to timing circuitry, which in turn will be connected to a suitable calculating means. Conveniently, the detection unit may include an interface for connecting to a digital controller, usually a microprocessor, which may be in the form of a general purpose personal computer. In this way, much of the timing and analytical function of the system of the present invention can be performed within the digital controller, with the specialized detection and sample conditioning functions being performed by the specialized apparatus of the present invention.

Figure 1:
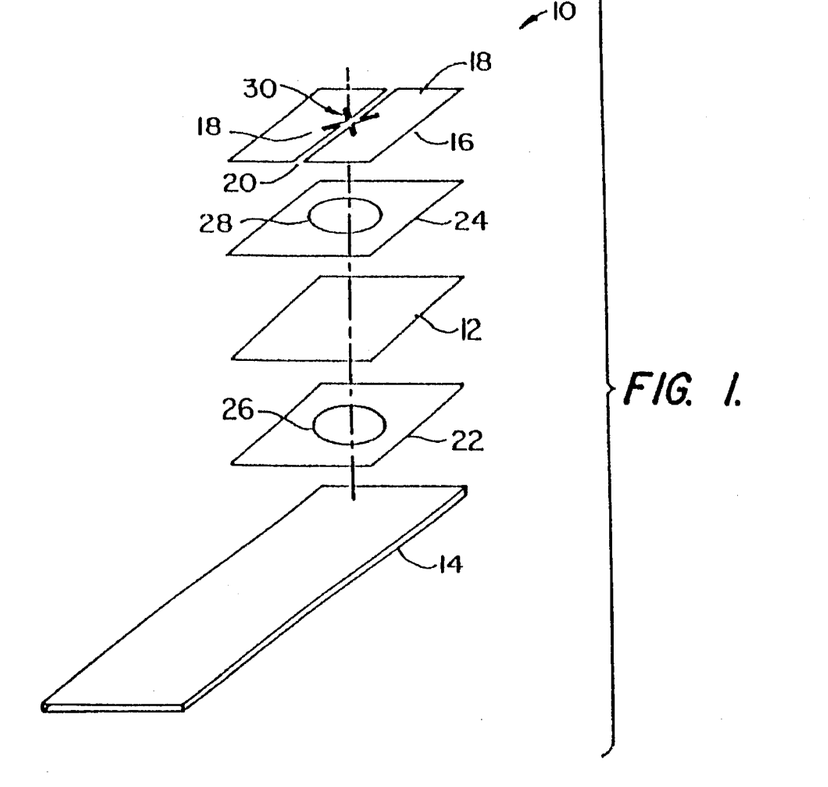
FIG. 1 is an exploded drawing of an exemplary embodiment of a test article constructed in accordance with the principles of the present invention.

Referring now to FIG. 1, an exemplary test article 10 constructed in accordance with the principles of the present invention will be described. The test article 10 includes a bibulous matrix structure 12, typically in the form of a flat membrane; a support structure 14, typically in the form of a transparent strip; and an electrode structure 16, typically comprising a pair of spaced-apart electrodes 18 separated by a gap 20. The membrane 12, support structure 14, and electrode structure 16 will be laminated together, for example by adhesive layers 22 and 24, as illustrated. The adhesive layers 22 and 24 will include central apertures 26 and 28 which permit viewing of the membrane 12 through the support structure 14 and application of sample to the membrane through the gap 20 in electrode structure 16. Preferably, the electrode structure 16 will include additional slots 30 formed in the electrodes 18, which slots define a target location for the application of liquid sample on the test article 10.

The bibulous matrix 12 will be composed of a material which can absorb liquid and which can contain, in dried form, the reagent(s) necessary for performing a desired assay. A wide variety of bibulous matrix materials might be used, including paper, methyl cellulose, porous polymers, and the like. The dimensions of bibulous matrix 12 should be such that at least a portion of the matrix can be saturated with liquid sample to both solubilize the necessary reagent(s) and to permit transport of the detectable reaction product to the lower side of the matrix so that it will be visible through the support structure 14.

In the preferred embodiment where small samples of blood are being analyzed, the bibulous matrix 12 will be a porous membrane structure composed of a hydrophilic (bibulous), non-swellable polymeric matrix material having pore dimensions which permit entry of blood plasma and proteins while excluding blood cells, particularly red blood cells (erythrocytes). The membrane should be composed of a single, continuous polymeric material with a foam-like structure consisting of a torturous network of channels having widths on the order of microns ($\mu m$). The torturous network of channels is "densely packed" in that the "void volume" occupied by the empty space of the channels is an appreciable percentage of the total membrane volume, typically 10% or greater. Since all reaction chemistry, and subsequent signal generation, takes place in the void volume, a high void volume is desirable for producing a strong signal. A torturous network of channels is desired over straight and direct pores, (such as the short, direct pores obtained with nucleopore membranes), as longer average channel lengths tend to produce an increasing isolation between the zone of the membrane where reaction chemistry is occurring, and the excess sample remaining on the surface of the membrane. This helps to render the system less sensitive to variations in applied sample volume.

In the specific case of blood coagulation assays, the porous membrane structure 12 will be impregnated with reagents necessary to induce coagulation in blood plasma which enters the interior of the porous matrix and to produce a detectable signal as an indication of the coagulation capability of the blood. It is particularly critical to the present invention that the polymeric matrix material of the porous membrane 12 be substantially free from interference with the coagulation pathway which is being induced. In particular, the polymeric matrix material should be free from surface effects, interactions, and artifacts which might induce coagulation or inactivate components such as enzymes, of the initiated pathway. Unintended initiation of a coagulation pathway could lead to false positive determinations while enzyme inactivation could lead to false negative determinations. It is therefore important that the polymeric matrix material have no promoting or diminishing effect on the coagulation reactions occurring within the membrane. Criteria can be for determining if a membrane is acceptable for use in coagulation testing are set forth in detail in U.S. Pat. No. 5,418,143 the full disclosure of which is incorporated herein by reference. A particularly preferred polymeric matrix material for performing blood coagulation assays is a 0.45 $\mu m$ asymmetric polysulfone membrane material available from Filterite-Memtec, 9690 Deeveco Road, Suite 7, Timonium, Md. 21093, Catalog No. BTS-25.

The region of bibulous matrix 12 which is beneath the sample application target location slots 30 will be the reaction zone. It is in this region that the matrix 12 is first wetted and where the actual chemical reaction which results in production of a detectable reaction product occurs. When used with very small samples, as described above, the reaction zone will typically be relatively small, frequently being 1 cm in diameter or less, often being less than 0.5 cm.

The remaining regions of the matrix 12 which are not wetted by the sample will not undergo a chemical reaction and will not accumulate visible reaction product.

Chemical reagents necessary for performing an assay according to the present invention will be impregnated within the bibulous matrix 12 and will be reconstituted by application of the liquid sample thereto. For the preferred enzymatic assays of the present invention, the reagents will include an enzyme substrate which is converted into an optically detectable product, typically a fluorescent, luminescent, or colored product, as a result of interaction with an enzyme. The enzyme may be the desired analyte or related to the analyte, or the enzyme may be added to the liquid sample and the production of detectable product by the enzyme modulated or otherwise affected by presence of analyte in the sample. The substrate may be a natural enzyme substrate which produces a natural detectable product, e.g. in the case of peroxidases, oxidases, hydrolases, and the like, or may be a synthetic substrate comprising a substrate group, such as a polysaccharide or peptide, which is cleavably linked to a reporter molecule, such as a chromogenic, chemiluminescent, or fluorogenic molecule. The presence or activity of the enzyme in the sample results in cleavage of the linker, causing a change in the optical characteristics of the reporter molecule. A variety of useful substrates are described in Haughland, *Molecular Probes Handbook of Fluorescent Probes in Research Chemicals*, Molecular Probes, Inc., Eugene, Oreg., the full disclosure of which is incorporated herein by reference.

In the exemplary case of blood coagulation assays, necessary reagents include a coagulation initiator which initiates a preselected event or stage in either an extrinsic or intrinsic coagulation pathway and a substrate which is activated by a component which is produced in a subsequent stage of the coagulation pathway. A buffer will also be provided to maintain the test pH within a range compatible with the coagulation pathway, and optional reagents include flow control agents which decrease the chromatographic separation of the various test components as blood plasma enters the membrane, cofactors which sustain or enhance the chemical reactions of the coagulation pathway, stability enhancers, and pigments which enhance the optical characteristics of the test article. Typically, these reagents will be combined in one or more aqueous solution(s) which are applied to all or a portion of the polymeric matrix material. The matrix material may then be dried or lyophilized (and optionally mounted on the handle 14) to form a test article having the reagents non-covalently adsorbed therein. In some cases, it may be possible to covalently attach at least some of the reagents, although covalent attachment will usually not be necessary. Particular coagulation inhibitors, substrates, buffers, coagulation cofactors, and fluid control agents are set forth in U.S. Pat. No. 5,418,143, the full disclosure of which has previously been incorporated herein by reference.

The support structure 14 may take a variety of forms. The support structure 14 is intended primarily to act as a physical support for the remaining components of the test article 10 and should be optically transmissive, preferably being completely transparent at the light wavelengths of interest to the assay protocol. In a preferred aspect of the present invention, the support structure 14 will also act as a moisture barrier in preventing loss of sample from the bibulous membrane 12. Suitable support structures 14 may be composed of transparent plastics, such as polystyrene, which is sufficiently thick and rigid to serve as a handle to permit manipulation of the test article 10 in the method steps of the present invention. Polystyrene strips having a length in the range from about 2 cm to 10 cm, a width in the range from about 0.5 cm to 2 cm, and a thickness in the range from about 0.1 mm to 0.5 mm have been found to be acceptable.

The electrode structure 16, is intended primarily to facilitate measurement of the electrical resistance across the reaction zone of bibulous matrix 12. It will be appreciated that the methods of the present invention could utilize electrical resistance probes which contact the bibulous matrix directly, that is without the need for providing intermediate contacting electrodes. The preferred test article 10 of the present invention, however, provides a suitable electrode structure in order to facilitate electrical resistance measurement using the detection unit, as described in more detail hereinafter.

The electrode structure 16 preferably also serves as a cover for the bibulous matrix 12 to inhibit evaporative and other losses of sample fluid therefrom. Thus, the electrode structure 16 will generally cover a majority of the exposed surface of the bibulous matrix 12, typically leaving only the small gap 20 and slots 30 therebetween.

Conveniently, both electrode halves 18 of the electrode structure 16 will be composed entirely of a conductive material, usually a metal foil. Use of the metal foil also acts to enhance heat transfer to the reaction zone of bibulous matrix 12, as described in more detail in connection with the detection unit hereinafter. It will be appreciated, however, that the individual electrodes 18 need not be composed entirely of electrically conductive material, and in fact only need to define a discrete conductive path from the bibulous matrix 12 to a location which can be probed or connected by the detection unit.

It should be further appreciated that the test articles of the present invention are not limited to structures having the electrode 16 and support structure 14 sandwiched about a bibulous matrix 12. Test articles according to the present invention require only that a pair of spaced-apart electrodes be provided on either side of a sample target location on the bibulous matrix, where the electrodes facilitate interconnection with a electrical resistance measuring mechanism, such as that provided by the detection unit of the present invention.

The adhesive layers 22, 24 may be composed of any suitable material, typically being double sided tape, such as that available from 3M Corporation, Minneapolis, Minn.

Figure 2:
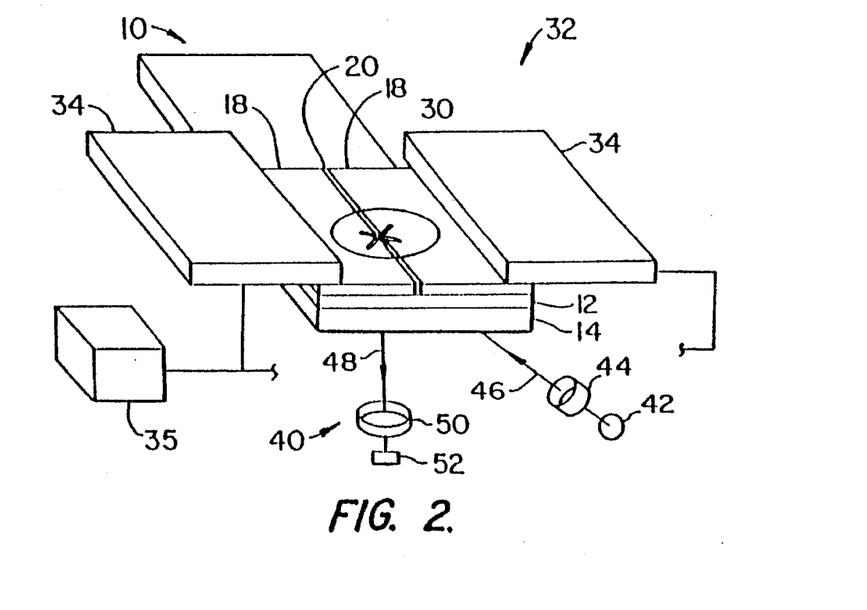
FIG. 2 is a schematic representation showing the test article in FIG. 1 present in a detection unit.

Referring now to FIG. 2, a detection unit 32 is schematically illustrated. The detection unit 32 includes plates 34 which contact the electrodes 18 of the test article 10 when the test article has been inserted into the detection unit. The contact plates 34 act as probes in measuring electrical resistance across the reaction zone in matrix 12 beneath the target location slots 30. Plates 34 will be connected to conventional electrical resistance monitoring circuitry in order to provide an output suitable for a digital control unit (not illustrated) or microprocessor.

In a preferred aspect of the present invention, plates 34 will be heated, typically by conventional electrical resistance heaters. For example, the plates 34 may have heating coils on the surface thereof or embedded therein. The heating coils, in turn, could be connected to a conventional power supply 35, with heat being controlled by conventional control circuitry or by a separate computer or other digital controller. Heat provided by plates 34 will be transferred by metallic electrode plates 18 to the matrix 12 to an area at least partially overlapping with the reaction zone.

Detection unit 32 further includes a system 40 for optically viewing the reaction zone when the test article 10 is in place within the unit. This optical system may monitor reflectance, fluorescence, or luminescence. In this example, a fluorescence system 40 is illustrated. This fluorescence system 40, as illustrated, includes a light source 42 and a notch filter 44 which together provide a light beam 46 which falls on the reaction zone of test article 10 through the transparent support structure 14. Reflected or emitted light 48 passes through a second notch filter 50, with filtered light being detected by photodetector 52. In the exemplary case of blood coagulation assays, detection will usually be based on fluorescence, where the light beam 46 is provided at an excitation wavelength and the light beam 48 is emitted at a known emission wavelength.

In summary, an assay according to the present invention may be performed by applying a liquid sample through the target location 30 on the electrode structure 16 of the test article 10. The liquid sample will flow through the gap 20 and other slots in the target location into a reaction zone within bibulous matrix 12. The presence of analyte in the sample will affect or modulate the production of a detectable reaction product within the matrix 12, eventually providing an optically detectable change on the lower surface of the matrix. The production of optically active reaction products may be observed by directing a light beam 46 through the transparent support 14 onto the reaction zone of membrane 12. The fluorescent material at present, will emit light at a fluorescent wavelength which is eventually detected by a photodetector 52. The amount of signal produced over time will depend on the amount of analyte present in the sample.

Figure 3:
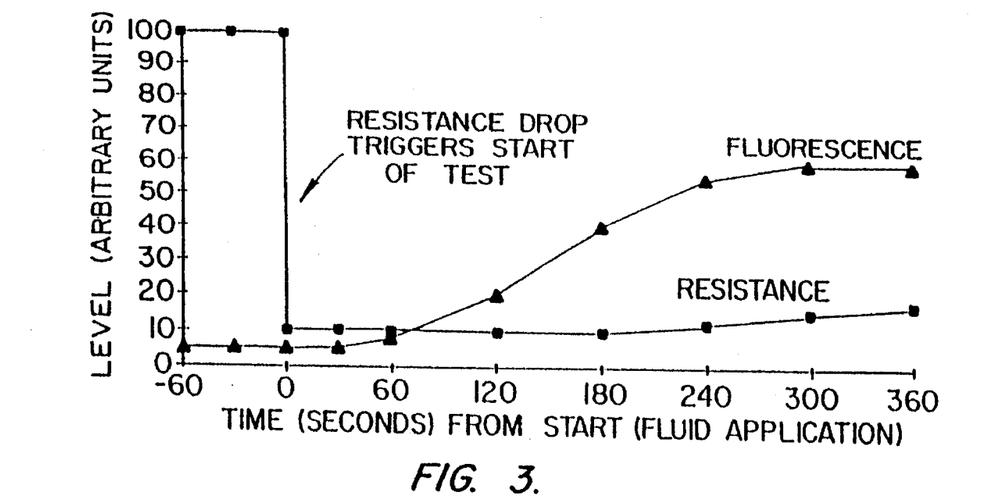
FIG. 3 is an exemplary graph showing the change in electrical and optical properties of a test article upon contact with analyte in a liquid sample.

FIG. 3 illustrates the changes in resistance and optical characteristics that typically take place during the course of an assay. Before the application of a fluid sample, the resistance across the electrode gap is extremely high. By contrast, the optical signal (here shown as fluorescence) is low. Upon application of sample at time zero, there is an immediate drop in resistance. By contrast, there is no corresponding change in the optical signal until appreciable amounts of the enzyme substrate have been converted to detectable product within the reaction membrane. As time continues, the resistance across the electrode junction on the reagent strip may increase, due to drying of the strip. As previously discussed, the system may choose to reject a particular sample as being insufficiently moist if the resistance measurement becomes too high.

The following examples are offered by way of illustration, not by way of limitation.

EXPERIMENTAL

General Methodology

Figure 4:
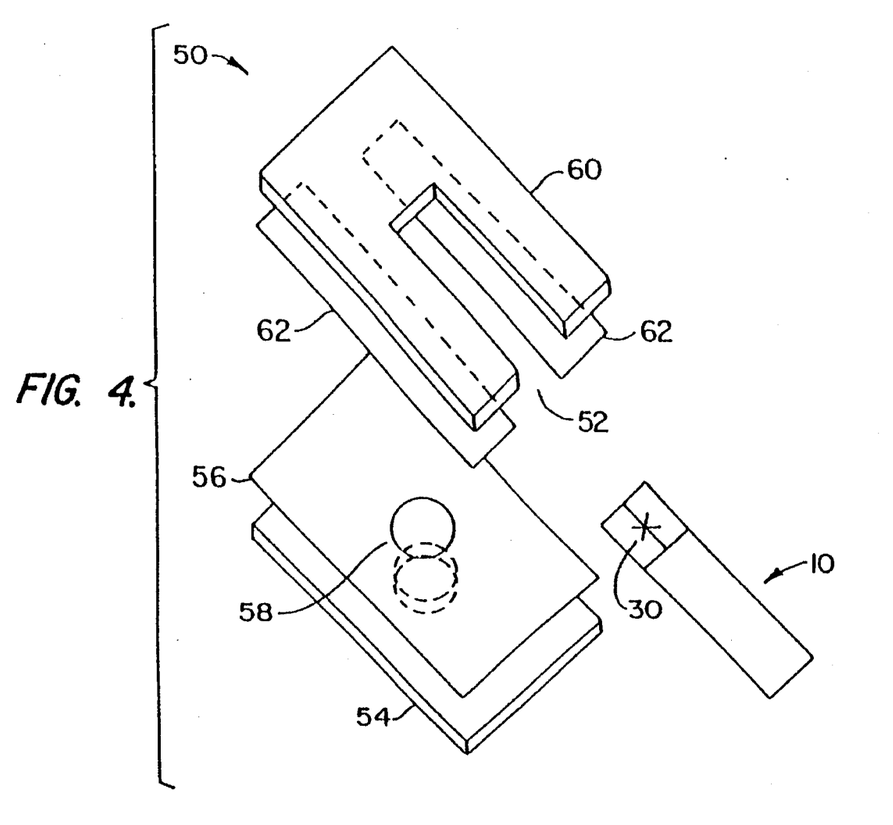
FIG. 4 illustrates the test article and detection unit utilized in the examples of the Experimental section.

Instrument:

Observations were performed using a prototype instrument. The instrument optics included a Siemens BPW-34B photodetector mounted below a 550 nanometer filter with a 25 nanometer bandwidth ($25-550-A, Corion Corporation, Holliston, Mass.). The specimens were illuminated by a Mini-Maglite™ LM3A001 light bulb (Mag Instrument Inc., Ontario, Calif.) with output filtered through a 500 nanometer filter with a 25 nanometer bandwidth (Cordon Corporation, $25-500-A). The output from the photodetector was amplified by an instrumentation amplifier (described on page 89 of the IC Users Casebook, 1988, by Joseph Car, Howard Samms & Company), digitized by a 12 bit analog to digital converter, and recorded on an IBM compatible personal computer. Temperature control was achieved by placing reagent strip 10 in a heated reagent stage 50, as shown in FIG. 4. The stage 50 included an upper heater and a lower heater with test strip 10 in the middle. A slot 52 was provided into the upper stage to facilitate insertion and removal of the strip 10 into the stage, and to provide easy sample access from the top. The stage was heated by eight, 200 ohm ¼ watt resistors connected in parallel. For the lower heater, four resistors were mounted on a thin circuit board 54 and were used to heat a 0,015" thick aluminum plate 56, with a 0.5" diameter hole 58 as an optics aperture. For the upper heater, four resistors were mounted on a circuit board 60 and used to heat two separate, and electrically isolated, 0.015" thick aluminum plates 62. Circuit board 60 additionally had a 0.45" by 1.5" opening 52 in it to allow easy application of sample to the reagent strip's aperture 30.

As shown in both FIG. 2 and FIG. 4, aluminum plates 62 on the stage's upper heater made a tight contact with the opposite sides of the test strip's foil surface electrodes. The stage's relatively thick aluminum plates acted to evenly distribute the heat emanating from the resistors, and helped insure good heat flow to the test strip's foil surface. The tight contact between the meter's aluminum plates, and the test strip's foil electrodes, was also used to form an electrical circuit that was used to detect the state of the strip's fluid detection sensor.

The temperature was regulated by monitoring the stage via an Acculex RTDR-2 temperature sensitive resistor (Keithley MetraByte Instruments Corp., Taunton Mass.). The electronics used to construct the fluid sensor and the temperature sensor are standard resistance monitoring circuits described on pages 55 and 62 of the Dascon-1 Manual, copyright 1983, by Metrabyte Corporation, Taunton, Mass. Unless otherwise noted, temperatures were maintained at 37° C. by a feedback control program monitored by an IBM compatible personal computer. The computer system controlled a switching circuit that energized the heater, using a 6 volt power source, whenever temperatures dropped below 37° C. In use, reagent strips were allowed to pre-equilibrate to 37° C. for a minimum of 60 seconds before sample was applied.

Preparation of Boc-Val-Pro-Aru-Rhodamine 110

Five grams of Boc-Val-Pro-OH (catalog A-2480) were purchased from Bachem Bioscience, Inc., Philadelphia Pa. This was conjugated onto (CBZ-Arg)2-Rhodamine-110 to produce (Boc-Val-Pro-Arg)2-Rhodamine 110 following the methods of Mangel, et. al. in U.S. Pat. No. 4,557,862 and U.S. Pat. No. 4,640,893. This formed the enzyme substrate used to detect thrombin production in the exemplary prothrombin time assay disclosed here.

Preparation of photo-etched electrode apertures

A etching pattern was prepared, consisting of a repeated series of the following configuration: one 0.625" long, 0.015" wide electrode gap, as shown as 20 on FIG. 1, and two 0.185" long, 0.007 wide fluid apertures shown as 30 on FIG. 1, arranged in a cross configuration on the center of the electrode gap, with each slit separated by an angle of 60° from the other slits. This pattern was etched onto 1 mil thick aluminum foil by Accutech, Inc., San Fernando, Calif. using conventional photo-etching techniques. The apertures were trimmed to a square 0.500"×0.500" configuration, with the aperture centered in the middle of this square.

Preparation of coated membrane

Coated membranes were prepared generally as described in copending application Ser. No. 07/874,667.

In a 20 ml vial, using a small magnetic stirrer, the following were combined:

6 ml 0.2 M HEPES pH 7.4;

2 ml H2O;

1 ml 100 mM CaCl2; and 500 mg Sigma poly vinyl alcohol P-8136;

and were stirred for about 2 hours until the PVA had totally dissolved.

One gram of Sigma protease-free bovine serum albumin A-3292 was added, and the mixture was allowed to stir for about 20 minutes until it had totally dissolved. A solution of 4.5 x concentrated Dade-C thromboplastin (Baxter B4216-20, Baxter Healthcare Corporation, Miami, Fla.), was prepared by adding 880 μl H2O to nominal 4 ml containers of thromboplastin. One ml of the concentrated (4.5 x) Dade-C thromboplastin was added to the dip and was stirred for 10 minutes. One ml of a concentrated (4 mg/ml) solution of fluorescent thrombin substrate dissolved in 50% isopropanol, 50% H2O was then added, and the resulting mixture stirred for 10 minutes.

Membrane dip

The large pore side (dull side) of a BTS-25 0.45 μm asymmetric polysulfone membrane (Memtec/Filterite Corporation, Timonium Md.) was rapidly coated with fresh dip, and the excess dip was gently squeegeed off. The coated membrane was immediately dried in a mechanical convection oven at 50° C. for 15 minutes. The membrane was then stored with desiccant under cool (4° C.) conditions until use.

Preparation of membrane strips

The reagent's support layer 14, FIG. 1, was composed of 10 mil thick transparent styrene. The various layers were held together by 0.5" wide 3M 415 double sided adhesive tape, made by the 3M Corporation. To hand-assemble the strips, two preliminary assemblies were first created. The first assembly consisted of a series of 0.25" diameter holes spaced 0.500" apart, pre-punched in the double sided adhesive tape. This adhesive tape 24, FIG. 1, was then applied to a length of foil containing a series of repeating apertures, each 0.500"0 apart. Excess foil, used to keep the repeating aperture structures intact in the absence of the adhesive tape, was then trimmed away, producing an "aperture tape" assembly with adhesive on one side, and a repeating series of electrode apertures on the other side. This was kept flat to keep the delicate electrode aperture structures intact.

A second preliminary assembly was created consisting of a strip of transparent styrene laminated with 3M 415 tape and a length of 0.5" wide treated reaction membrane. To avoid migration of adhesive into the reaction membrane, and it's possible deleterious effects on storage, a series of 0.25" holes were punched every 0.500" in the sections of the tape that were immediately below the "reaction zone" on the final strip 22, FIG. 1. Thus the coated membrane in the reaction zone did not come into immediate contact with any materials except the metallic foil aperture covering. The two preliminary assemblies were then aligned with the aid of a light box, and laminated together. The repeating subunits on the final assembly were then cut into individual strips for testing.

This reagent, and the meter described previously, were then used to perform the following experiments.

Experiment 1

Resistance drop upon addition of biological fluids: Reagent strips were prepared according to the above methods. The resistance across the strips was monitored as a function of time. Before addition of blood, the resistance across the electrode junction was effectively infinite (>100 mega ohms). Upon addition of blood, the resistance immediately dropped to about 30 kilo ohms.

Experiment 2

Detection of insufficient sample by resistance readings. Reagent strips prepared according to above methods were each given 1.0, 2.0, 3.0, and 4.0 μl of whole blood. After six minutes of reaction time, the respective resistance measurements of the various strips were:

| Sample Size | Resistance |
| --- | --- |
| 1.0 μl | 2.5 mega ohms |
| 2.0 μl | 400K kilo ohms |
| 3.0 μl | 60K kilo ohms |
| 4.0 μl | 40K kilo ohms |

Insufficient sample thus could be detected by a substantial increase in resistance.

Experiment 3

Effect of metal foil on reaction kinetics at low humidity: Strips were prepared omitting the metallic foil, and studied with Sigma coagulation control I, II and III plasma in a low ambient humidity environment and manual initiation of test timing. In the absence of the surface covering, lower fluorescence intensity developed, and the reaction kinetics for level II and level III (prolonged and very prolonged PT time controls) was significantly prolonged.

Experiment 4

Effect of a hole in the transparent reagent support on reaction kinetics at low humidity: Strips were prepared containing the metallic foil, but additionally with a 0.25" diameter hole placed in the transparent support immediately below the reaction zone on the membrane. These were studied with coagulation control I, II and III plasma (C-7916, C-8916 and C-9916, Sigma Chemical Company, St. Louis, Mo.) in a low ambient humidity environment. In the absence of the surface covering, lower fluorescence intensity developed, and the reaction kinetics for level II and level III (prolonged and very prolonged PT time controls) was significantly prolonged.

Experiment 5

Effect of metallic foil cover on temperature eguilibration of reagent: Before they are applied to the meter, the test samples may be at a variety of different initial temperatures (typically 15°–30° C.). To give accurate results, the test article must equilibrate these different samples to the same reaction temperature (typically 37° C.) as rapidly as possible. This experiment measured the relative effectiveness of a metallic foil cover, versus a non-metallic plastic cover, at rapidly eguilibrating different samples.

In this experiment, a series of test articles were made up with either 1 mil thick aluminum covers, or 5 mil thick transparent styrene covers. These were placed into a meter stage and eguilibrated to 37° C. 10 μl drops of water (at 4° C.) were then applied, and the temperatures monitored by a non-contact infrared thermometer (C-1600 meter, Linear Laboratories Company, Fremont, Calif.). Both the aluminum foil and the transparent styrene were painted flat black (Model 2529 marker, Testor Corp., Rockford Ill.), to provide equivalent conditions for the infrared beam. The resulting temperatures were:

| Time after application (sec.) | Foil temp. | Plastic temp. |
| --- | --- | --- |
| 1 | 33 | 20 |
| 5 | 35 | 23 |
| 10 | 37 | 26 |
| 15 | 37 | 28 |
| 30 | 37 | 33 |
| 45 | 37 | 37 |

The results show that the foil covering equilibrated the sample to the desired temperature more quickly than did the plastic covering.

Experiment 6

Performing fluorescence assays without a meter hatch: In the following experiment, the meter was programmed to take fluorescence measurements by turning its light source on briefly every 15 seconds, and recording the fluorescence value. Immediately before the meter's own light source was turned on, however, the meter also recorded a "background" value. This background value was then subtracted from each fluorescence measurement.

It was found that when a non-light transmissive covering with a narrow slit was used, such as the metal foil arrangement discussed previously, the system was remarkably insensitive to the presence or absence of external light—e.g. normal room lighting, or indirect sunlight. This is attributed to a combination of factors, including the great attenuation of ambient light by the metal foil covering on the strip, the high fluorescence efficiency and amounts of the Rhodamine 110 fluorophore used in this experiment, and the background subtracting algorithm used here.

Experiment 7

Clinical study: Venous blood from 27 patients, including 20 patients being treated with Coumadin, was drawn and stored in citrate. 10 μl samples of whole blood from each patient were then run on the device as described above. Fluorescence measurements were taken every 15 seconds for six minutes. The time required for the fluorescence intensity to reach half maximum (T50%) was plotted versus the reference prothrombin times as determined on a MLA Electra 750 coagulation meter. A regression analysis was done using Microsoft Excel 4.0 software.

Figure 5:
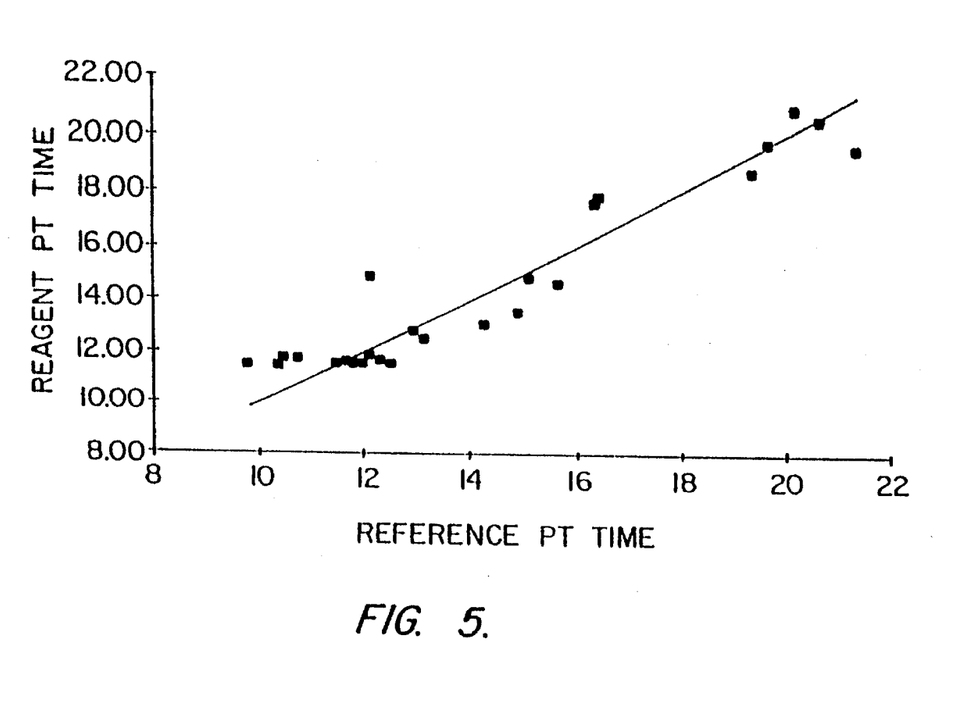
FIG. 5 is the result from an experiment using the test article and detection unit shown in FIG. 4. In this experiment, the results from 27 blood samples with varying prothrombin times were compared with prothrombin times obtained from a standard reference system.

A best fit polynomial to relate the T50% levels to the reference instrument was found to be prothrombin time (corrected)=1.93+0.079* T50%. The correlation coefficient ($R^2$) was 0.92. The results from this experiment are shown in FIG. 5. The results show that this configuration can give good clinical results.

Although the foregoing invention has been described in some detail by way of illustration and example, for purposes of clarity of understanding, it will be obvious that certain changes and modifications may be practiced within the scope of the appended claims.

What is claimed is:

1. A detection unit comprising:

a support stage for receiving a test article, the test article having spaced-apart electrodes in electrical contact with a reaction zone, wherein the reaction zone on the test article is disposed at a viewing location;

a heater attached to the support stage for heating the test article in the region of the reaction zone;

means attached to the support stage for detecting electrical resistance across the test article;

means attached to the support stage for optically viewing the reaction zone when disposed at the viewing location;

means in communication with the electrical resistance detecting means for initiating a timing cycle when the electrical resistance detecting means detects a lowering of electrical resistance across the test article upon application of a fluid sample having an amount of analyte therein to the test article;

means for actuating the optical viewing means and the electrical resistance detecting means at one or more times during the timing cycle to measure one or more optically detectable signals and electrical resistance values at known times during the timing cycle; and means for correlating the measured signals and values from the optical viewing means and the electrical resistance detecting means with the known times at which the signals and values are measured so that the amount of analyte initially present in the sample may be determined.

2. A detection unit as in claim 1, further comprising an input/output interface for connecting at least one of the heater, electrical resistance detection means, and the optical viewing means to a digital controller.

3. A detection unit as in claim 1, wherein the heater comprises an upper heated surface and a lower heated surface, which surfaces are disposed to contact a top and a bottom side of the test article around the reaction zone.

4. A detection unit as in claim 1, wherein the electrical resistance detecting means includes a pair of spaced-apart plates which contact the test article on opposite sides of the reaction zone when the test article is in place in the support stage.

5. A detection unit as in claim 1, wherein the optically viewing means comprises a light source which directs light at the reaction zone and a light detector which detects light from the reaction zone.

6. A detection unit as in claim 5, wherein the light source emits light at a wavelength selected to induce fluorescence in a particular reaction product and the light detector detects light at the fluorescent wavelength.

7. A detection unit for use in combination with a test article comprising:

(a) a bibulous matrix;

(b) one or more dried reagents which are present within the matrix and which, when wetted by a liquid sample, initiate an optically detectable chemical reaction with an analyte present in the sample;

(c) a pair of spaced-apart metal strips proximate a sample target location of the matrix, wherein the metal strips are disposed so that application of the liquid sample to the target location will lower electrical resistance between the electrode wherein the detection unit comprises:

a support stage for receiving the test article, where a reaction zone on the test article is disposed at a viewing location;

a heater attached to the support stage for heating the test article in the region of the reaction zone;

means attached to the support stage for detecting electrical resistance across the test article;

means attached to the support stage for optically viewing the reaction zone when disposed at the viewing location;

means in communication with the electrical resistance means for initiating a timing cycle when the electrical resistance detecting means detects a lowering of electrical resistance between the electrodes upon application the sample to the test article;

means for actuating the optical viewing means and the electrical resistance detecting means at one or more times during the timing cycle to measure one or more optically detectable signals and electrical resistance values at known times during the timing cycle; and means for correlating the measured signals and value from the optical viewing means and the electrical resistance detecting means with the known times at which the signals and values are measured so that the amount of analyte initially present in the sample may be determined.

8. A detection unit as in claim 7, further comprising an input/output interface for connecting at least one of the heater, electrical resistance detection means, and the optical viewing means to a digital controller.

9. A detection unit as in claim 7, wherein the heater comprises a pair of metal plates and means for heating said plates, wherein said plates contact the metal strips on the test article and said metal strips conduct heat to the reaction zone.

10. A detection unit as in claim 7, the electrical resistance detecting means includes the same metal plates which comprise the heater, whereby electrical resistance is measured across the gap between the metal strips on the test article.

11. A detection unit as in claim 7, wherein the optically viewing means comprises a light source which directs light at the reaction zone and a light detector which detects light from the reaction zone.

12. A detection unit as in claim 11, wherein the light source emits light at a wavelength selected to induce fluorescence in a particular reaction product and the light detector detects light at the fluorescent wavelength.

* * * * *